(12) United States Patent
Oh et al.

(10) Patent No.: US 10,591,437 B2
(45) Date of Patent: Mar. 17, 2020

(54) SOLID ELECTROLYTE-TYPE CARBON DIOXIDE SENSOR HAVING REDUCED INFLUENCE FROM VOLATILE ORGANIC COMPOUNDS

(71) Applicants: Hyundai Motor Company, Seoul (KR); Kia Motors Corporation, Seoul (KR); NANOIONICS KOREA CO., LTD., Gangneung-si (KR)

(72) Inventors: Sun-Mi Oh, Whasung-Si (KR); Hyun-Soo Sohn, Whasung-Si (KR); Jong-Min Kwon, Whasung-Si (KR); Yang-Ki Kim, Whasung-Si (KR); Tae-Won Lee, Whasung-Si (KR); Ji-Hye Kim, Whasung-Si (KR)

(73) Assignees: Hyundai Motor Company, Seoul (KR); Kia Motors Corporation, Seoul (KR); NANOIONICS KOREA CO., LTD., Gangneung-si (KR)

( * ) Notice: Subject to any disclaimer, the term of this patent is extended or adjusted under 35 U.S.C. 154(b) by 241 days.

(21) Appl. No.: 15/730,395

(22) Filed: Oct. 11, 2017

(65) Prior Publication Data
US 2018/0252669 A1 Sep. 6, 2018

(30) Foreign Application Priority Data
Mar. 6, 2017 (KR) ........................ 10-2017-0028176

(51) Int. Cl.
*G01N 27/407* (2006.01)
*G01N 33/00* (2006.01)

(52) U.S. Cl.
CPC ..... *G01N 27/4074* (2013.01); *G01N 27/4071* (2013.01); *G01N 27/4075* (2013.01); *G01N 33/004* (2013.01); *Y02A 50/249* (2018.01)

(58) Field of Classification Search
CPC .............. G01N 33/004; G01N 27/407; G01N 27/4071; G01N 27/4074; G01N 27/4073; G01N 27/4075
See application file for complete search history.

(56) References Cited

U.S. PATENT DOCUMENTS 5,194,134 A * 3/1993 Futata ................ G01N 27/4074
204/416

FOREIGN PATENT DOCUMENTS

| JP | 08-201340 A | * | 8/1996 | ........... G01N 27/416 |
| JP | 11-30603 A | * | 2/1999 | ........... G01N 27/416 |

OTHER PUBLICATIONS

JPO computer-generated English language translation of the Description section of Japanese patent application H09-200990 downloaded Aug. 21, 2019 (Year: 1999).*

(Continued)

*Primary Examiner* — Alexander S Noguerola
(74) *Attorney, Agent, or Firm* — Morgan, Lewis & Bockius LLP

(57) ABSTRACT

A solid electrolyte-type $CO_2$ sensor having a reduced influence from volatile organic compounds (VOCs), includes: a solid electrolyte; a reference electrode which is formed at one side of the solid electrolyte; a detecting electrode of which one side is joined and which is formed at the other side of the solid electrolyte; a substrate which is formed at the other side of the reference electrode; and an oxidation catalyst which is formed at the other side of the detecting electrode.

14 Claims, 11 Drawing Sheets

(56) References Cited

OTHER PUBLICATIONS

JPO computer-generated English language translation of the Description section of Japanese patent application H07-031822 downloaded Aug. 22, 2019 (Year: 1996).*

Liu et al., "Recent Advances in Preferential Oxidation of CO Reaction over Platinum Group Metal Catalysts," ACS Catal. 2012, 3, 1165-1178 (Year: 2012).*

Barshad et al., "A Dynamic Study of CO Oxidation on Supported Platinum," AIChE Journal (vol. 31, No. 4) Apr. 1985, pp. 649-658 (Year: 1985).*

* cited by examiner

SOLID ELECTROLYTE-TYPE CARBON DIOXIDE SENSOR HAVING REDUCED INFLUENCE FROM VOLATILE ORGANIC COMPOUNDS

CROSS-REFERENCE TO RELATED APPLICATIONS

The present application claims priority to Korean Patent Application No. 10-2017-0028176, filed on Mar. 6, 2017, the entire contents of which is incorporated herein for all purposes by this reference.

BACKGROUND OF THE INVENTION

Field of the Invention

The present invention relates to a solid electrolyte-type $CO_2$ sensor having a reduced influence from volatile organic compounds (VOCs), and more particularly, to a solid electrolyte-type $CO_2$ sensor having a reduced influence from VOCs, in which the accuracy of the sensor is improved as a result of a reduced influence caused by the VOCs by including an oxidation catalyst.

Description of Related Art

Automobiles are a means of transportation, which is essential for human life, and make life richer and more convenient. Recently, automobiles have become more high-end, various options have been added, and among them, technologies for constructing a safe driving system of the automobile have been studied. As efforts to create a comfortable environment for safe driving have been accelerated, alternatives including replacement of components applied to the seats of vehicles with materials which emit less carcinogens have been suggested, and among them, interests in the quality of air inside the vehicle are increasing and much attention has been paid to carbon dioxide ($CO_2$). Carbon dioxide affects humans in a sealed volume in various ways, is a factor negatively affecting driving, and is responsible for reducing the driver's brain activity and causing drowsiness. Accordingly, the real-time monitoring of the concentration of carbon dioxide for safe driving of vehicles and the function of monitoring and suppressing the environment for causing drowsy driving in real time in connection with the air conditioning system of vehicles in addition to that has drawn attention. Consequently, there is a need for a sensor for measuring the concentration of carbon dioxide, and as a solution to the need for the sensor, optical (non-dispersive infrared: NDIR) sensors, semiconductor-type gas sensors, and home or universal sensors in a solid electrolyte system have been suggested.

Meanwhile, carbon dioxide is a gas whose concentration is difficult to measure as a chemically very stable gas in the atmosphere. The optical sensor is most frequently used as a sensor for detecting the carbon dioxide, and the present system is a system in which light with a specific wavelength of an emitted laser is absorbed by carbon dioxide in the air, the reduced intensity of light is sensed, and the amount of carbon dioxide is measured. The present device has an advantage in that selectivity, quantitativeness, and reproducibility are excellent, but has problems in that a hermetically sealed volume is required for measurement, and the volume is large and the weight is very heavy due to the physical sizes of constituent elements and filters. In particular, since the driving part and the measurement device are very expensive and the configuration of the processing part for control is complex, the price of the overall measurement equipment is definitely high, and accordingly, the present device fails to be widely utilized even though the use thereof is very diverse.

As another system for measuring the concentration of carbon dioxide, a semiconductor-type gas sensor using a semiconductor compound such as $SnO_2$ or $TiO_2$ is used, and uses a principle of measuring the concentration of the gas through a change in resistance displayed when gas particles are adsorbed on the surface of the semiconductor compound. In the present case, there is an advantage in that a sensor in the form of a thin film-type device can be manufactured, but there is also a disadvantage in that the gas selectivity significantly deteriorates because it is difficult to differentiate different gas particles to be adsorbed, and accordingly, it is difficult to use the semiconductor-type gas sensor as a device to select and measure only carbon dioxide.

A solid electrolyte-type gas sensor in the related art has a problem in that due to the problems including a decrease in the concentration of oxygen atoms adsorbed onto the surface of a detecting electrode as a result of a reaction between volatile organic compounds (VOCs) and the detecting electrode, the sensor is affected by the VOCs, and accordingly, the sensing performance and accuracy of the sensor deteriorate. Furthermore, due to VOCs, and the like generated from vehicles, solid electrolyte-type gas sensors applied to vehicles have a problem in that the concentration of a gas to be sensed cannot be measured. Therefore, there is a need for developing a solid electrolyte $CO_2$ sensor capable of exactly measuring the concentration of a gas to be sensed without being affected by VOCs.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a solid electrolyte-type $CO_2$ sensor having a reduced influence of volatile organic compounds (VOCs), in which the sensing performance of the sensor is improved by reducing an influence of the volatile organic compounds on the solid electrolyte-type gas sensor due to the inclusion of an oxidation catalyst.

The technical problems which the present invention intends to solve are not limited to the technical problems which have been mentioned above, and still other technical problems which have not been mentioned will be apparently understood by a person with ordinary skill in the art from the description of the present invention.

Various aspects of the present invention are directed to providing a solid electrolyte-type $CO_2$ sensor having a reduced influence from volatile organic compounds (VOCs), the sensor including: a solid electrolyte; a reference electrode which is formed at one side of the solid electrolyte; a detecting electrode of which one side is joined and which is formed at the other side of the solid electrolyte; a substrate which is formed at the other side of the reference electrode; and an oxidation catalyst which is formed at the other side of the detecting electrode.

In an exemplary embodiment of the present invention, the reference electrode may be a mixture of Li(Na)—Ti(Fe)—O or Pt.

In an exemplary embodiment of the present invention, the detecting electrode may be any one of $A_2CO_3$ or a mixture of $A_2CO_3$ and $BCO_3$, A may be Li or Na, and B may be Ba, Ca, or Sr.

In an exemplary embodiment of the present invention, the solid electrolyte may be $Na_{1+x}Zr_2Si_xP_{3-x}O_{12}$ and $0<X<3$.

In an exemplary embodiment of the present invention, the solid electrolyte may be $Li_{2+2x}Zn_{1-x}GeO_4$ and $0<X<1$.

In an exemplary embodiment of the present invention, the substrate may be alumina or mullite.

In an exemplary embodiment of the present invention, the oxidation catalyst may be a metal catalyst.

In an exemplary embodiment of the present invention, the metal catalyst may include any one or more of Pt, Rh, or Pd.

In an exemplary embodiment of the present invention, the oxidation catalyst may be a supported catalyst in which a metal is supported on ceramic powder.

In an exemplary embodiment of the present invention, the supported metal may have a BET of 80 to 300 $m^2/g$.

In an exemplary embodiment of the present invention, a thickness of the ceramic powder applied may be three times or more than a particle size of the supported metal, and may be 1,000 μm or less.

In an exemplary embodiment of the present invention, a weight of the supported metal may be 0.5 wt % or more based on a weight of the supported catalyst.

In an exemplary embodiment of the present invention, a ceramic powder of the supported catalyst may be any one of $Al_2O_3$, $ZrO_2$, $CeO_2$, $TiO_2$, zeolite, or a mixture thereof, and the metal may be any one of Pt, Rh, Pd, or a mixture thereof.

In an exemplary embodiment of the present invention, the oxidation catalyst may be a ceramic catalyst.

In an exemplary embodiment of the present invention, the ceramic catalyst may include any one or more of $Al_2O_3$, $CuCrO_2$, $Cu_2CrO_4$, $ZrO_2$, $CeO_2$, $TiO_2$, or zeolite.

In an exemplary embodiment of the present invention, the oxidation catalyst may seal the detecting electrode.

In an exemplary embodiment of the present invention, the reference electrode may be joined and sealed by bonding the solid electrolyte to the substrate.

According to a solid electrolyte-type $CO_2$ sensor of the present invention, there is an effect of providing a solid electrolyte-type carbon dioxide sensor having a reduced influence from volatile organic compounds (VOCs), in which the sensing performance of the sensor is improved by reducing an influence of the volatile organic compounds on the solid electrolyte-type gas sensor.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
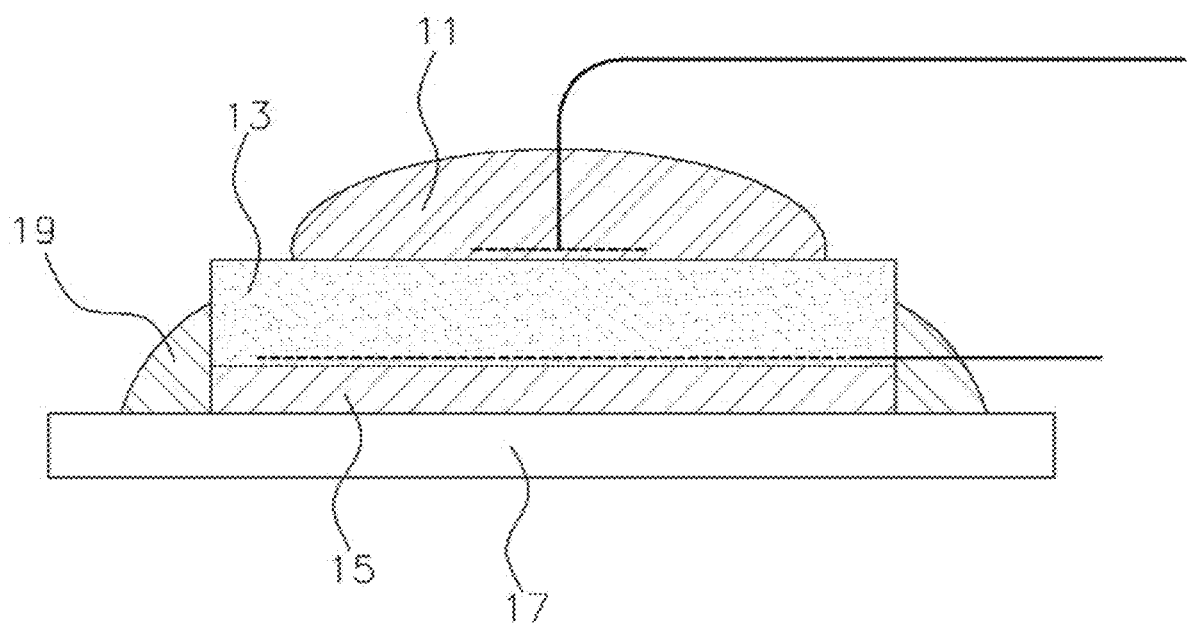
FIG. 1 is a configuration view of a solid electrolyte-type carbon dioxide sensor according to the related art.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Interior materials disposed inside a vehicle or seats of a vehicle, and the like include numerous volatile organic compounds (VOCs) composed of carbon or hydrogen, and the like, and furthermore, numerous wallpapers and interior materials used in households also include volatile organic compounds. These volatile organic compounds and the like emit a large amount of volatile organic compounds inside vehicles or into the interior of households. Further, aromatics and the like used to make interiors of vehicles or houses comfortable include a large amount of volatile organic compounds.

The volatile organic compounds significantly affect solid electrolyte-type carbon dioxide sensors in the related art. When specifically examined, there is a problem in that volatile organic compounds emitted into interior volumes react with a detecting electrode of the solid electrolyte-type carbon dioxide sensor to increase the concentration of carbon dioxide present in the interior or decrease the concentration of oxygen present in the interior, thereby degrading the sensing performance of the sensor. Consequently, to increase the accuracy of the solid electrolyte-type carbon dioxide sensor, it is important to develop a solid electrolyte-type carbon dioxide sensor which is not influenced by the volatile organic compounds.

Various embodiments of the present invention relate to a solid electrolyte-type carbon dioxide sensor having a reduced influence from volatile organic compounds (VOCs). Specifically, the present invention is directed to solve the above-described problems in the related art and provides a solid electrolyte-type carbon dioxide sensor having a reduced influence from VOCs, the sensor including: a solid electrolyte 103; a reference electrode 105 which is formed at one side of the solid electrolyte 103; a detecting electrode 101 of which one side is joined and which is formed at the other side of the solid electrolyte 103; a substrate 107 which is formed at the other side of the reference electrode 105; and an oxidation catalyst 111 which is formed at the other side of the detecting electrode 101.

Figure 2:
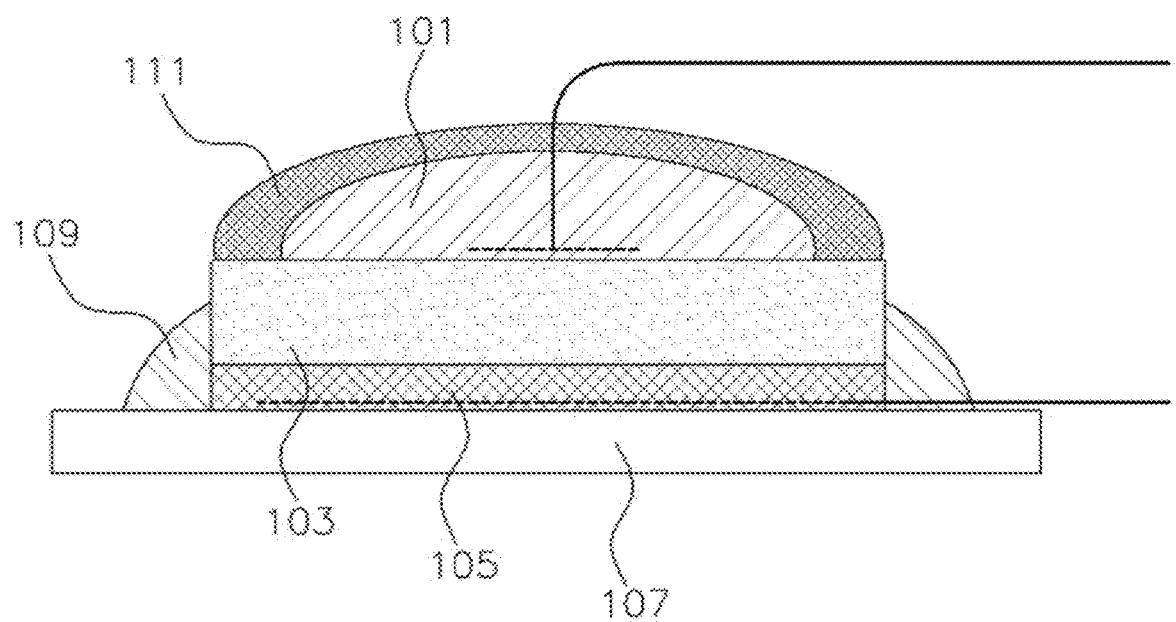
FIG. 2 is a configuration view of a solid electrolyte-type carbon dioxide sensor according to an exemplary embodiment of the present invention.

When more specifically examined, FIG. 1 is a configuration view of a solid electrolyte-type carbon dioxide sensor according to the related art. In the solid electrolyte-type carbon dioxide sensor in the related art, a substrate 17, a reference electrode 15, a solid electrolyte 13, and a detecting electrode 11 are stacked subsequently. Additionally, the solid electrolyte-type carbon dioxide sensor in the related art may further include a sealing material 19 wherein the reference electrode is not exposed to the outside. FIG. 2 is a configuration view of a solid electrolyte-type carbon dioxide sensor according to an exemplary embodiment of the present invention. As illustrated in FIG. 2, in the solid electrolyte-type $CO_2$ sensor having a reduced influence from VOCs according to an exemplary embodiment of the present invention, a substrate 107, a reference electrode 105, a solid electrolyte 103, a detecting electrode 101, and an oxidation catalyst 111 may be stacked in this order, and additionally, the solid electrolyte-type $CO_2$ sensor having a reduced influence from VOCs according to an exemplary embodiment of the present invention may further include a sealing material 109 wherein the reference electrode is not exposed to the outside.

In an exemplary embodiment of the present invention, the reference electrode 105 is preferably a mixture of Li(Na)—Ti(Fe)—O or Pt, and the detecting electrode 101 is any one of $A_2CO_3$ or a mixture of $A_2CO_3$ and $BCO_3$, A is Li or Na, and B is Ba, Ca, or Sr.

Furthermore, in an exemplary embodiment of the present invention, the solid electrolyte 103 is $Na_{1+X}Zr_2Si_XP_{3-X}O_{12}$, and $0<X<3$, and the solid electrolyte 103 is $Li_{2+2X}Zn_{1-X}GeO_4$, and $0<X<1$. Further, the substrate 107 is preferably alumina or mullite.

In an exemplary embodiment of the present invention, the oxidation catalyst 111 is preferably a metal catalyst. Additionally, the metal catalyst preferably includes any one of Pt, Rh, or Pd, and the oxidation catalyst 111 is preferably a supported catalyst in which a metal is supported on a ceramic powder. Further, the ceramic powder of the supported catalyst is any one of $Al_2O_3$, $ZrO_2$, $CeO_2$, $TiO_2$,—zeolite, or a mixture thereof, and the metal is any one of Pt, Rh, Pd, or a mixture thereof. Furthermore, the oxidation catalyst 111 is preferably a ceramic catalyst, the ceramic catalyst preferably includes any one or more of $Al_2O_3$, $CuCrO_2$, $Cu_2CrO_4$, $ZrO_2$, $CeO_2$, $TiO_2$, or zeolite, and the oxidation catalyst 111 preferably seals the sensing electrode 101.

First, when a theoretical background of a solid electrolyte-type carbon dioxide is explained, the detecting electrode, the reference electrode, and the overall electrode reaction are as in the following Chemical Formulae 1 to 3. Further, in the following Chemical Formulae, A corresponds to Na or Li.

Sensing electrode: $2A+CO_2+O_{ads} \rightarrow A_2CO_3$ [Chemical Formula 1]

Reference electrode: $2A+\tfrac{1}{2}O_2 \rightarrow A_2O$ [Chemical Formula 2]

Overall electrode reaction: $A_2O+CO_2+O_{ads} \rightarrow A_2CO_3+\tfrac{1}{2}O_2$ [Chemical Formula 3]

Chemical Formula 1 shows a half battery reaction of a detecting electrode, Chemical Formula 2 shows a half battery reaction of a reference electrode, and Chemical Formula 3 shows an overall electrode reaction in which the half battery reaction of the detecting electrode and the half battery reaction of the reference electrode are synthesized. When a voltage is obtained by applying Chemical Formula 3, the following Equation 1 is obtained.

$$V = -\frac{RT}{2F}\ln \alpha_{CO_2} + \frac{1}{2F}\left[\Delta G^{rxn.} + RT \ln\frac{\alpha_{A_2CO_3}}{\alpha_{A_2O}} + RT \ln\frac{\alpha_{O_2}^{1/2}}{\alpha_{O_{ads}}}\right]$$
$$= -C \log \alpha_{CO_2} + \left[D + C \log\frac{\alpha_{O_2}^{1/2}}{\alpha_{O_{ads}}}\right]$$
[Equation 1]

In Equation 1, $\Delta G^{rxn.}$ corresponds to a reaction energy of the overall electrode reaction, and $\Delta G^{rxn.}$ may be expressed as the following Equation 2.

$$\Delta G^{rxn} = \Delta G_{A_2O}{}^f + \Delta G_{CO_2}{}^f - \Delta G_{A_2CO_3}{}^f$$ [Equation 2]

$\Delta G_f$ corresponds to a formation free energy. Further, in Equation 1, $a_{CO_2}$ denotes the activity of carbon dioxide, and is proportional to the concentration of carbon dioxide. Further, $a_{A2CO3}$ denotes the activity of $A_2CO_3$, and has a predetermined value in an isothermal state. Furthermore, $a_{A2O}$ denotes the activity of $A_2O$, and has a predetermined value in an isothermal state. Consequently, when these are synthesized, C of Equation 1 corresponds to an ideal gas constant, a Faraday constant, and a value of the absolute temperature, so that when these values are summarized, C of Equation 1 corresponds to a positive constant. Further, D of Equation 1 corresponds to a positive constant value because $a_{A2CO3}$ and $a_{A2O}$ have a predetermined value in an isothermal state, and correspond to the summary of absolute temperature and positive constant values.

Therefore, according to Equation 1, the activities of oxygen adsorbed and oxygen present in the air are the same as each other, that is, $a_{O_2}^{1/2}$ and $a_{O_{ads}}$ are the same as each other, and as a result, the equation may be summarized as the following Equation 3, and it can be confirmed that $a_{O_2}^{1/2}$ and $a_{O_{ads}}$ are just proportional to the log value of the concentration of carbon dioxide, that is, the activity of carbon dioxide, which is proportional to the concentration of carbon dioxide.

$$V = -C \log a_{CO_2} + D \quad \text{[Equation 3]}$$

Therefore, it can be confirmed that a solid electrolyte carbon dioxide sensor is influenced by the concentration of carbon dioxide, that is, the activity of carbon dioxide.

Figure 3:
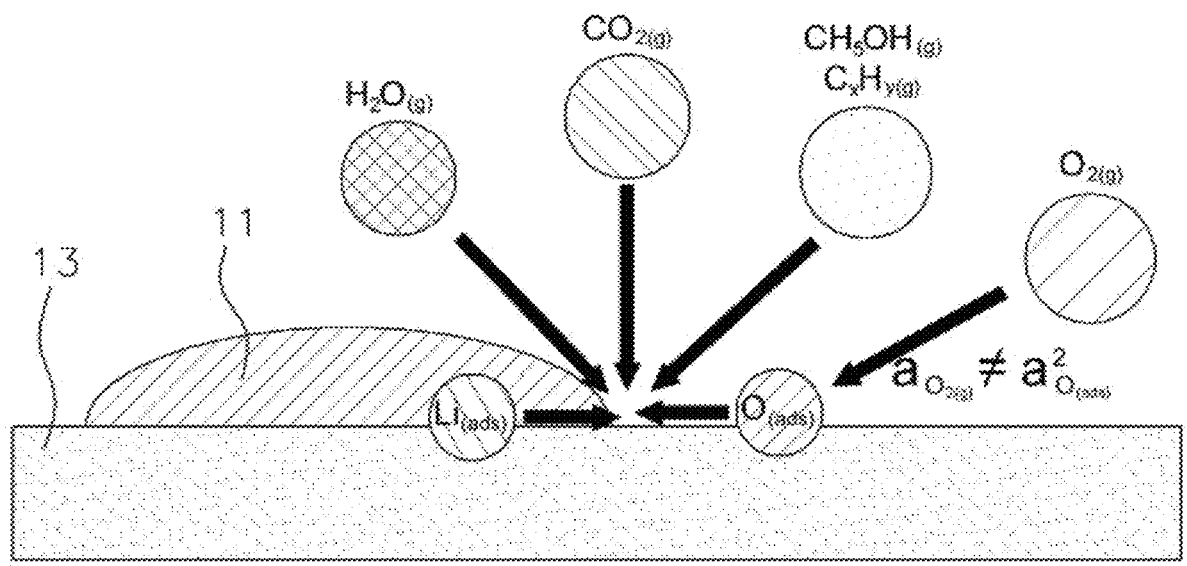
FIG. 3 is a schematic view illustrating reactions of the solid electrolyte-type carbon dioxide sensor according to the related art and volatile organic compounds.

Meanwhile, when a theoretical background in which a solid electrolyte-type carbon dioxide sensor in the related art is influenced by volatile organic compounds is examined, FIG. 3 is a schematic view illustrating reactions of the solid electrolyte-type carbon dioxide sensor according to the related art and volatile organic compounds. According to an oxidation reaction including the following Chemical Formulae 4 and 5 of the volatile organic compounds, the concentration of oxygen adsorbed becomes lower than the concentration of oxygen present in the atmosphere because oxygen atoms adsorbed are consumed. Consequently, the signal of the solid electrolyte-type carbon dioxide sensor is increased toward the positive direction, and for the present reason, there is a problem in that the concentration of carbon dioxide present in the atmosphere is underestimated. That is, an oxidation reaction of a representative ethanol in the volatile organic compounds is shown in the following Chemical Formula 4, and also, an oxidation reaction of a general hydrocarbon compound is shown in the following Chemical Formula 5.

$$C_2H_5OH_{(g)} + 3O_{2(g)} \rightarrow \quad \text{[Chemical Formula 4]}$$
$$C_2H_5OH_{(g)} + 6O_{(ads)} \rightarrow \ldots \rightarrow 2CO_{2(g)} + 3H_2O_{(g)}$$

$$C_xH_{y(g)} + \left(x + \frac{y}{4}\right)O_{2(g)} \rightarrow \quad \text{[Chemical Formula 5]}$$
$$C_xH_{y(ads)} + \left(2x + \frac{y}{2}\right)O_{(ads)} \rightarrow \ldots \rightarrow xCO_{2(g)} + \frac{y}{2}H_2O_{(g)}$$

That is, when carbon dioxide has a predetermined concentration in the reaction of the volatile organic compounds, according to the Le Chatelier's principle, oxygen atoms adsorbed are decreased and carbon dioxide and water are increased according to the increase in concentration of volatile organic compounds. Accordingly, it can be confirmed that the equations have a relationship including the following Equations 4 and 5. In the following Equation 4, $\Delta a_{CO2}$ denotes an increment of carbon dioxide, and in the following Equation 5, $\Delta a_{O(ads)}$ corresponds to a decrement of oxygen atoms adsorbed.

$$\frac{\Delta a_{CO_2}}{a_{CO_2}} \approx 0 \quad \text{[Equation 4]}$$

$$0 < \frac{\Delta a_{O_{(ads)}}}{a_{O_{(ads)}}} = \frac{\Delta a_{O_{(ads)}}}{a_{O_2}^{1/2}} < 1 \quad \text{[Equation 5]}$$

Accordingly, when it is assumed that the carbon dioxide is present at a predetermined concentration, Equation 4 becomes 0 because $\Delta a_{CO2}$ in Equation 4 corresponds to approximately 0. Furthermore, the concentration of oxygen atoms adsorbed is decreased because the oxygen atoms adsorbed react with the volatile organic compounds, and accordingly, it can be confirmed that the concentration of oxygen atoms adsorbed is decreased as compared to the concentration of oxygen adsorbed before the reaction. Accordingly, it can be confirmed that the value in Equation 5 is present as a value between 0 and 1.

When the aspect of the voltage of a solid electrolyte-type carbon dioxide sensor is explained according to the conditions, the voltage comes down to the following Equation 6 when the voltage of a solid electrolyte-type carbon dioxide sensor in the related art given in Equation 3 is assumed as $V^{ideal}$ and the voltage is determined by putting values into Equation 3 in consideration of $\Delta a_{CO2}$ and $\Delta a_{O(ads)}$ which are changed by the organic compounds to measure the voltage ($V^{voc,w/o\ Cat.}$) which is changed by the volatile organic compounds in the solid electrolyte-type carbon dioxide sensor in the related art.

$$V^{VOC,w/o\ Cat.} = \quad \text{[Equation 6]}$$
$$-C\log(a_{CO_2} + \Delta a_{CO_2}) + \left[D + C\log\frac{a_{O_2}^{1/2}}{a_{O_2}^{1/2} - \Delta a_{O_{(ads)}}}\right]$$

The determination of a subtraction between $V^{voc,w/o\ Cat.}$ and $V^{ideal}$ comes down to the following Equation 7.

$$V^{ideal} - V^{VOC,w/o\ Cat.} = \quad \text{[Equation 7]}$$
$$C\left[\log\left(\frac{a_{CO_2} + \Delta a_{CO_2}}{a_{CO_2}}\right) + \log\frac{a_{O_2}^{1/2} + \Delta a_{O_{ads}}}{a_{O_2}^{1/2}}\right]$$

When Equation 4 and Equation 5 are put into Equation 7,

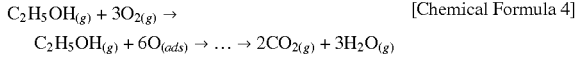

consequently becomes 0, and

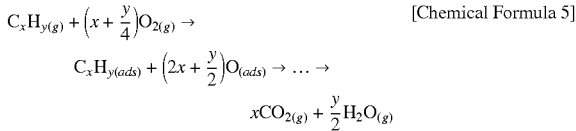

results in having a negative value.

Therefore, a voltage of the solid electrolyte-type carbon dioxide sensor in the related art results in $V^{voc,w/o\ Cat.} > V^{ideal}$, and the concentration of carbon dioxide converted from the voltage is actually determined as a value lower than the concentration of carbon dioxide because the voltage of the sensor is increased.

Figure 4:
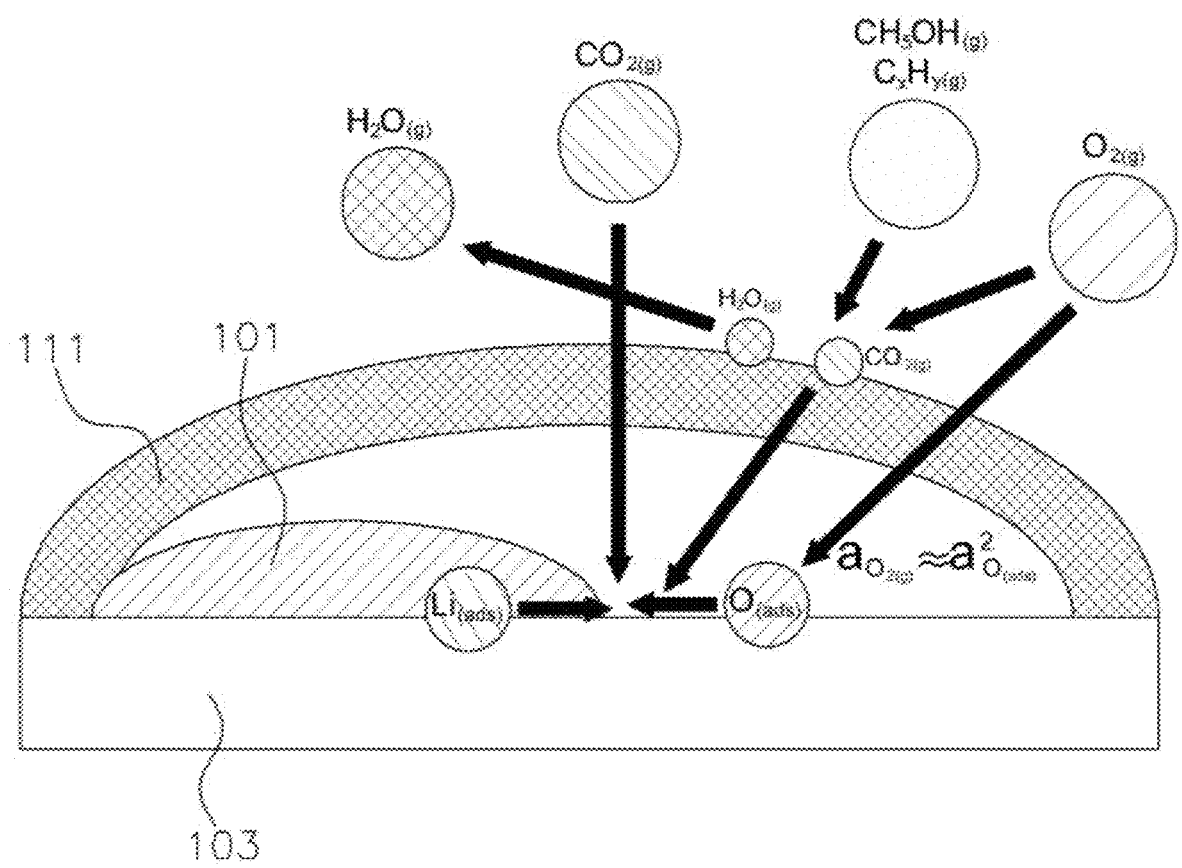
FIG. 4 is a schematic view illustrating reactions of the solid electrolyte-type carbon dioxide sensor according to an exemplary embodiment of the present invention and volatile organic compounds.

Meanwhile, when a theoretical background in which the solid electrolyte-type carbon dioxide sensor having a reduced influence from VOCs according to an exemplary embodiment of the present invention has a reduced influence from the volatile organic compounds is examined, FIG. 4 is a schematic view illustrating reactions of the solid electrolyte-type carbon dioxide sensor according to an exemplary embodiment of the present invention and volatile organic compounds. The sensor of the present invention further includes an oxidation catalyst, and as a result, volatile organic compounds react in the oxidation catalyst as in Chemical Formulae 4 and 5. Due to the reaction, water fails to pass through the oxidation catalyst and is emitted into the atmosphere, and oxygen atoms adsorbed onto a reference electrode react with carbon dioxide in the atmosphere and carbon dioxide increased due to the reaction without reacting with the volatile organic compounds. Therefore, a relationship including the following Equation 8 may be derived.

$$\frac{\Delta a_{CO_2}}{a_{CO_2}} = \frac{\Delta a_{O_2}}{a_{O_{(ads)}}^2} \approx 0 \qquad \text{[Equation 8]}$$

In Equation 8, $\Delta a_{CO2}$ denotes an increment of carbon dioxide, and $\Delta a_{O2}$ denotes a decrement of oxygen. Consequently, Equation 8 has a value of approximately 0 because there is no decrement of oxygen.

When the aspect of the voltage of a solid electrolyte-type carbon dioxide sensor having a reduced influence from VOCs according to an exemplary embodiment of the present invention is explained according to the conditions, the voltage comes down to the following Equation 9 when the voltage of a solid electrolyte-type carbon dioxide sensor in the related art given in Equation 3 is assumed as $V^{ideal}$ and the voltage is determined by putting values into Equation 3 in consideration of $\Delta a_{CO2}$ and $\Delta a_{O2}$ which are changed by the organic compounds to measure the voltage ($V^{voc,w/o\ Cat.}$) which is changed by the volatile organic compounds in the solid electrolyte-type carbon dioxide sensor having a reduced influence from VOCs according to an exemplary embodiment of the present invention, that is, the sensor including an oxidation catalyst.

$$V^{ideal} - V^{VOC,w/o\ Cat.} = C\left[\log\left(\frac{a_{CO_2} + \Delta a_{CO_2}}{a_{CO_2}}\right) + \log\frac{a_{O_2}^{1/2} + \Delta a_{O_2}^{1/2}}{a_{O_2}^{1/2}}\right] \qquad \text{[Equation 9]}$$

When the conditions of Equation 8 are put into Equation 9, the $$\log\frac{a_{O_2}^{1/2} + \Delta a_{O_2}^{1/2}}{a_{O_2}^{1/2}}$$

term in Equation 9 corresponds to 0, and the $$\log\left(\frac{a_{CO_2} + \Delta a_{CO_2}}{a_{CO_2}}\right)$$

term becomes a positive value because the concentration of carbon dioxide is increased.

Therefore, a voltage of the solid electrolyte-type carbon dioxide sensor having a reduced influence from VOCs according to an exemplary embodiment of the present invention comes down to $V^{voc,w/o\ Cat.} < V^{ideal}$, and the concentration of carbon dioxide converted from the voltage is determined as a value higher than the actual concentration of carbon dioxide because the voltage of the sensor is decreased.

Consequently, in the case of a solid electrolyte-type carbon dioxide sensor including no oxidation catalyst, volatile organic compounds react with oxygen adsorbed onto a reference electrode, so that the concentration of oxygen adsorbed is decreased, and as a result, the voltage is increased. Therefore, there is a problem in that the concentration of carbon dioxide included in the atmosphere is underestimated.

In contrast, in the case of a solid electrolyte-type carbon dioxide sensor including an oxidation catalyst of the present invention, the amount of volatile organic compounds present in vehicles, more specifically, volatile organic compounds produced by aromatics present in vehicles is equal to or less than several tens of ppm, so that the voltage becomes constant because the amount of carbon dioxide produced by the reactions of the oxidation catalyst and the volatile organic compounds is minimal as compared to the concentration of carbon dioxide in the atmosphere, and as a result, the amount of carbon dioxide produced does not significantly influence the voltage.

In an exemplary embodiment of the present invention, the supported metal preferably has a BET of 80 to 300 $m^2/g$. When a BET of a metal of a solid electrolyte-type carbon dioxide sensor according to an exemplary embodiment of the present invention, which is supported on ceramic powder, that is, a specific surface area of a supported material is 80 to 300 $m^2/g$, there is no difference according to the surface area. Furthermore, when the temperature is 170° C. or more, which is a temperature lower than the operation temperature of the solid electrolyte-type carbon dioxide sensor of the present invention, the supported metal preferably has a BET of 80 to 300 $m^2/g$ because volatile organic compounds exhibit 100% conversion rate.

In an exemplary embodiment of the present invention, a thickness of the ceramic powder applied is three times or more than a particle size of the supported metal, and is 1,000 µm or less. Specifically, the thickness of metal supported on the ceramic powder applied is three times or more than the size of the metal particles, and does not exceed 1,000 µm. There is a problem in that when the thickness of metal supported on the ceramic powder applied is more than 1,000 µm, the catalyst effect may vary due to the temperature gradient, and when the metal is applied in a thickness three times less than the size of the particles, carbon dioxide and the oxidation catalyst are not sufficiently reacted with each other.

In an exemplary embodiment of the present invention, a weight of the supported metal is preferably 0.5 wt % or more based on a weight of the supported catalyst. In the case of a metal supported on ceramic powder, a weight of the metal, that is, a supported amount of metal supported on ceramic powder is preferably 0.5 wt % or more. When the supported amount is less than 0.5 wt %, the supported amount is not sufficient, and as a result, it is required that the conversion rate of volatile organic compounds, that is, production of carbon dioxide and water by reaction of volatile organic compounds with the supported catalyst is decreased, or the production conditions are high temperature conditions. However, in the case of the solid electrolyte-type carbon dioxide sensor having a reduced influence from VOCs according to an exemplary embodiment of the present invention, due to the conditions where the temperature is maintained at approximately 400° C., a sufficient VOC conversion rate is exhibited when the weight of the supported metal is 0.5 wt % or more, and as a result, the weight of the supported metal is preferably 0.5 wt % or more based on the weight of the supported catalyst.

In an exemplary embodiment of the present invention, the reference electrode is joined and sealed by bonding the solid electrolyte to the substrate. The reference electrode has improved attaching property and durability while being hermetically sealed with the substrate and the solid electrolyte, and does not cause cracks, thereby having an effect in that the reliability for measuring the concentration of carbon dioxide is improved by moisture because it is possible to prevent the reference electrode from reacting with moisture by perfectly blocking moisture from permeating through the reference electrode.

Examples

Hereinafter, the present invention will be described in more detail through the Examples. These Examples are only for exemplifying the present invention, and it will be obvious to those skilled in the art that the scope of the present invention is not interpreted to be limited by these Examples.

Comparative Example 1 being the related art is composed of platinum (Pt) as a reference electrode, $Li_2CO_3$—$BaCO_3$ as a detecting electrode, NASICON ($Na_3Zr_2Si_2PO_{12}$) as a solid electrolyte, and alumina as a substrate, and the reference electrode is a solid electrolyte-type carbon dioxide sensor sealed by using a sealing material. Further, Comparative Example 2 being the related art is composed of platinum (Pt) as a reference electrode, $Li_2CO_3$—$BaCO_3$ as a detecting electrode, NASICON ($Na_3Zr_2Si_2PO_2$) as a solid electrolyte, and alumina as a substrate, and the reference electrode is a solid electrolyte-type carbon dioxide sensor joined and sealed by bonding the solid electrolyte to the substrate.

Figure 5:
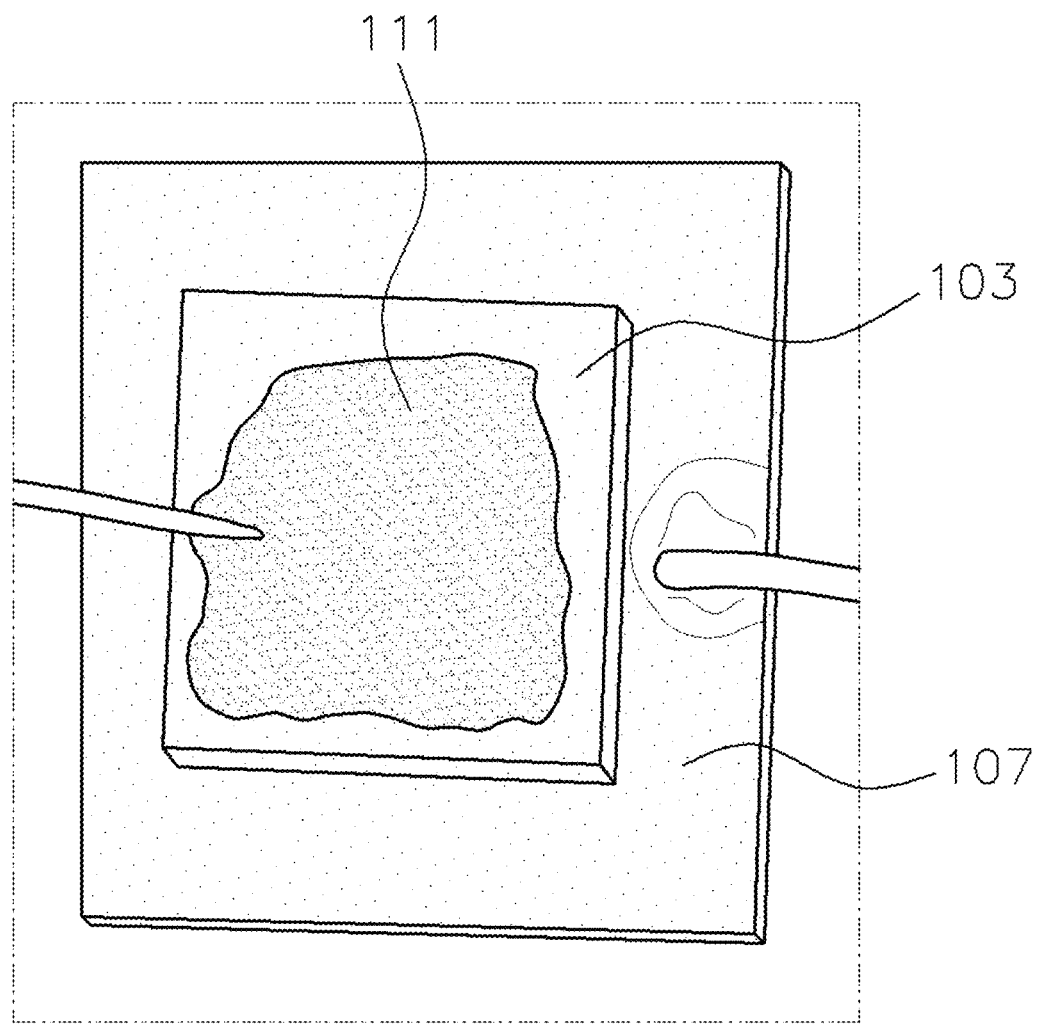
FIG. 5 is a photograph of a solid electrolyte-type carbon dioxide sensor according to an exemplary embodiment of the present invention.

In contrast, FIG. 5 is a photograph of a solid electrolyte-type carbon dioxide sensor according to an exemplary embodiment of the present invention. As illustrated in FIG. 5, the Example being the present invention is a solid electrolyte-type carbon dioxide sensor having a reduced influence from VOCs, which includes platinum (Pt) as a reference electrode, $Li_2CO_3$—$BaCO_3$ as a detecting electrode, NASICON ($Na_3Zr_2Si_2PO_{12}$) as a solid electrolyte, alumina as a substrate, and platinum supported on alumina, which is a supported catalyst as an oxidation catalyst, and preferably, the reference electrode is joined and sealed by bonding the solid electrolyte to the substrate.

In the preparation method in the Example of the present invention, a platinum paste being a reference electrode is applied onto a substrate, and then is dried. And then, NASICON being a solid electrolyte is stacked on the reference electrode. Thereafter, $Li_2CO_3$—$BaCO_3$ being the detecting electrode is stacked, and a platinum paste supported on alumina, which is an oxidation catalyst, is applied onto the detecting electrode, and then is dried. Thereafter, a heat treatment is carried out at approximately 595° C. for approximately 5 minutes. Further, to reduce the influence of the mixture on the reference electrode, when necessary, the reference electrode is sealed with a sealing material to be protected to the outside.

To measure the influence of volatile organic compounds on an exemplary embodiment of the present invention and the Comparative Examples being the related art, an aromatic from which volatile organic compounds are generated in excess was used.

Figure 6:
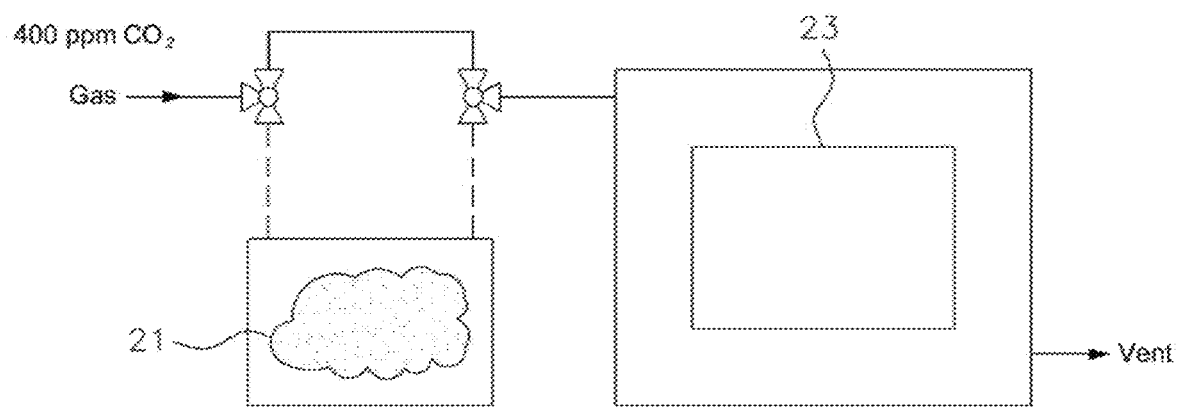
FIG. 6 is a schematic view illustrating an aspect for measuring voltage over time in a state where volatile organic compounds are blocked in an exemplary embodiment of the present invention and the comparative example of the related art.
Figure 7:
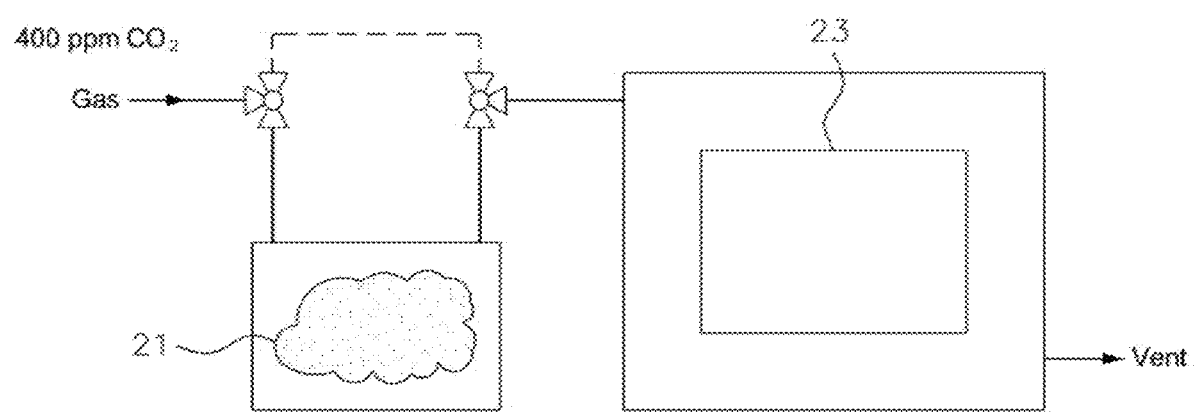
FIG. 7 is a schematic view illustrating an aspect for measuring voltage over time in a state where volatile organic compounds are injected in an exemplary embodiment of the present invention and the comparative example of the related art.

FIG. 6 is a schematic view illustrating an aspect for measuring voltage over time in a state where volatile organic compounds are blocked in an exemplary embodiment of the present invention and the comparative example of the related art. Further, FIG. 7 is a schematic view illustrating an aspect for measuring voltage over time in a state where volatile organic compounds are injected in an exemplary embodiment of the present invention and the comparative example of the related art. As illustrated in FIG. 6 and FIG. 7, air having a carbon dioxide concentration of 400 ppm was injected according to the given configuration. FIG. 6 illustrates that the injected air passes through a solid electrolyte-type carbon dioxide sensor 23 present in a chamber without going through an aromatic 21. FIG. 7 illustrates that the injected air passes through a solid electrolyte-type carbon dioxide sensor 23 present in a chamber while going through an aromatic 21. The volume of the chamber corresponds to 150 mL, and the flow of the air corresponds to 100 sccm. Further, the maintenance time was set to 2 hours. Additionally, as the aromatic 21, Aromatic 1 (trade name: Febreeze Car-Clear Sky Wind, manufacturer: Zobele Instrument Shenzhen, Co. Ltd.) and Aromatic 2 (trade name: Angel Wing-White, manufacturer: INTBIZ Corporation) were used.

Figure 8:
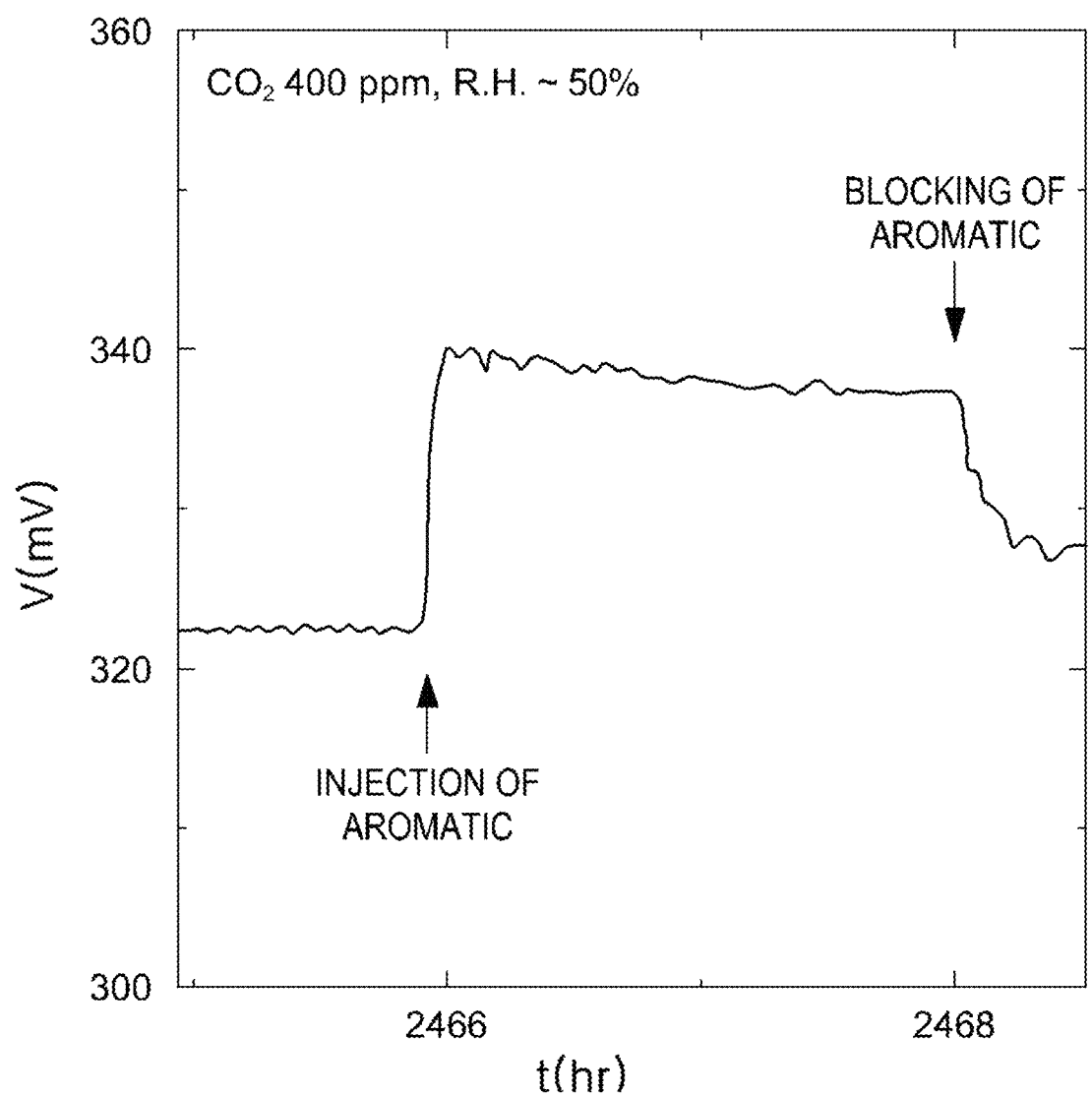
FIG. 8 is a graph illustrating voltage over time to determine an influence of Aromatic 1 in Comparative Example 2, which is the related art.

FIG. 8 is a graph illustrating voltage over time to determine an influence from Aromatic 1 in Comparative Example 2, which is the related art. The ambient conditions during the evaluation procedure are as follows: the concentration of carbon dioxide is 400 ppm, and the relative humidity is 50%. When Aromatic 1 was injected as illustrated in FIG. 8, the voltage was increased by approximately 20 mV as compared to the case before Aromatic 1 was injected, and the increase corresponds to the case where the concentration of carbon dioxide is underestimated by approximately half the value.

Figure 9:
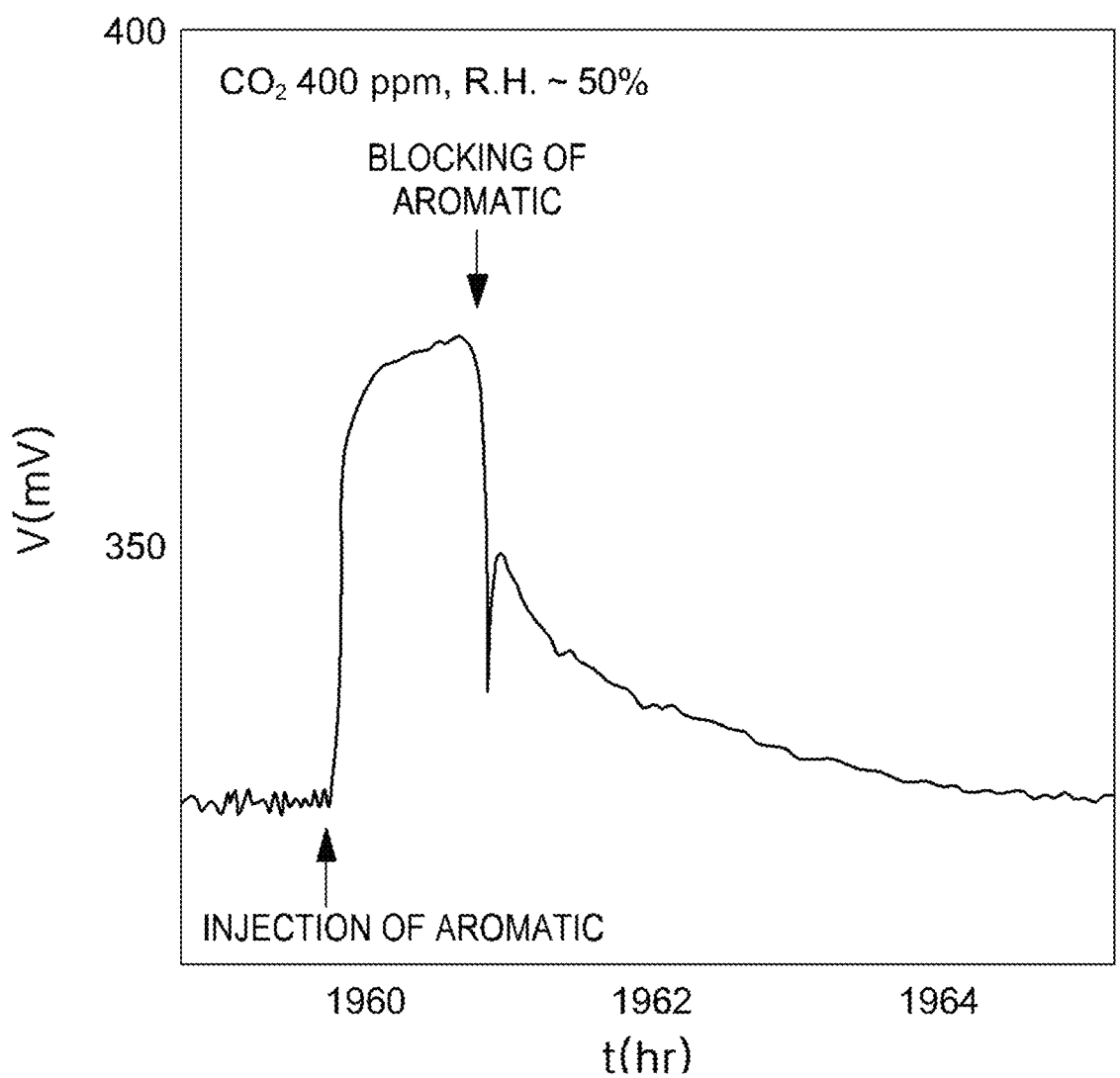
FIG. 9 is a graph illustrating voltage over time to determine an influence of Aromatic 2 in Comparative Example 2, which is the related art.

FIG. 9 is a graph illustrating a voltage over time to determine an influence from Aromatic 2 in Comparative Example 2, which is the related art. The ambient conditions during the evaluation procedure are as follows: the concentration of carbon dioxide is 400 ppm, and the relative humidity is 50%. As illustrated in FIG. 9, in Aromatic 2, the content of volatile organic compounds is higher than that in Aromatic 1. It can be confirmed that at the instance when Aromatic 2 is injected, the voltage is increased by approximately 50 mV or more, and from the confirmation, it can be confirmed that the concentration of carbon dioxide is underestimated to approximately one tenth, and as a result, the sensor fails to serve as a solid electrolyte-type carbon dioxide sensor.

Figure 10:
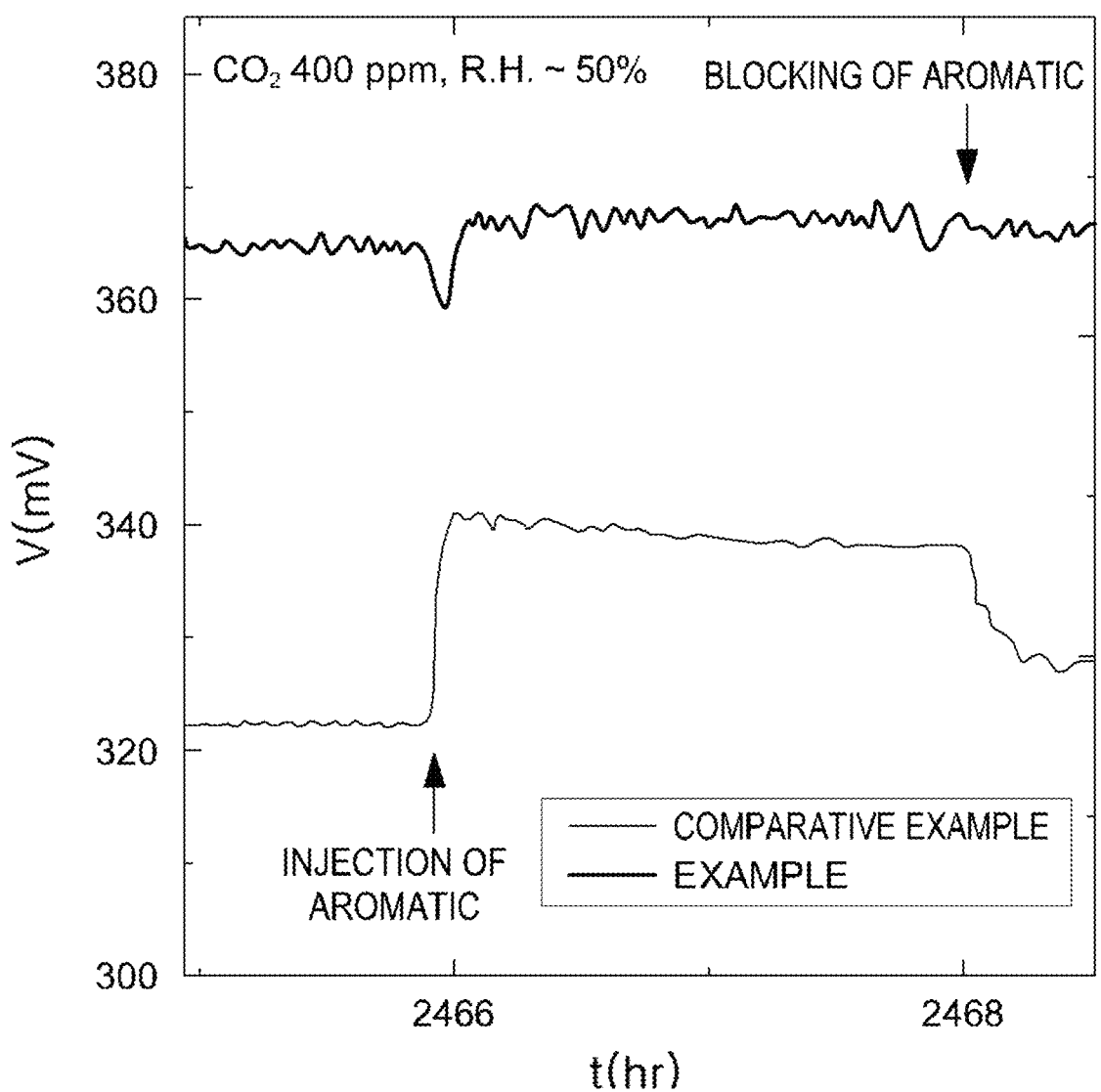
FIG. 10 is a graph illustrating voltage over time before and after Aromatic 1 is injected into the solid electrolyte-type carbon dioxide sensors in Comparative Example 2 being the related art and the Example of the present invention.

FIG. 10 is a graph illustrating voltage over time before and after Aromatic 1 is injected into the solid electrolyte-type carbon dioxide sensors in Comparative Example 2 being the related art and the Example of the present invention. The ambient conditions during the evaluation procedure are as follows: the concentration of carbon dioxide is 400 ppm, and the relative humidity is 50%. It can be confirmed that at the instance when Aromatic 1 is injected, the Example of the present invention has nearly no change in voltage, whereas Comparative Example 2 being the related art has an increase in voltage by approximately 20 mV or more. Furthermore, it can be confirmed that even at the instant when Aromatic 1 is blocked from being injected, the Example of the present invention has no change in voltage, whereas Comparative Example 2 being the related art has a voltage which gradually returns to the voltage before Aromatic 1 is injected. In the Example of the present invention, it can be confirmed that at the instance when Aromatic 1 is injected, the amount of volatile organic compounds generated from the aromatic corresponds to a range of several to several tens of ppm, and as a result, the amount of carbon dioxide generated by reacting the volatile organic compounds with an oxidation catalyst is minimal, and thus, does not significantly influence the signal. More specifically, it can be confirmed that when the concentration of volatile organic compounds is within a range of several to several tens of ppm, the amount of carbon dioxide generated by reacting the volatile organic compounds with an oxidation catalyst is minimal, and as a result, there occurs an error within 10% in voltage as in the Example of FIG. 10 by a solid electrolyte-type carbon dioxide sensor, but the error in voltage is minimal, and as a result, there is no problem with measuring the concentration of carbon dioxide.

Figure 11:
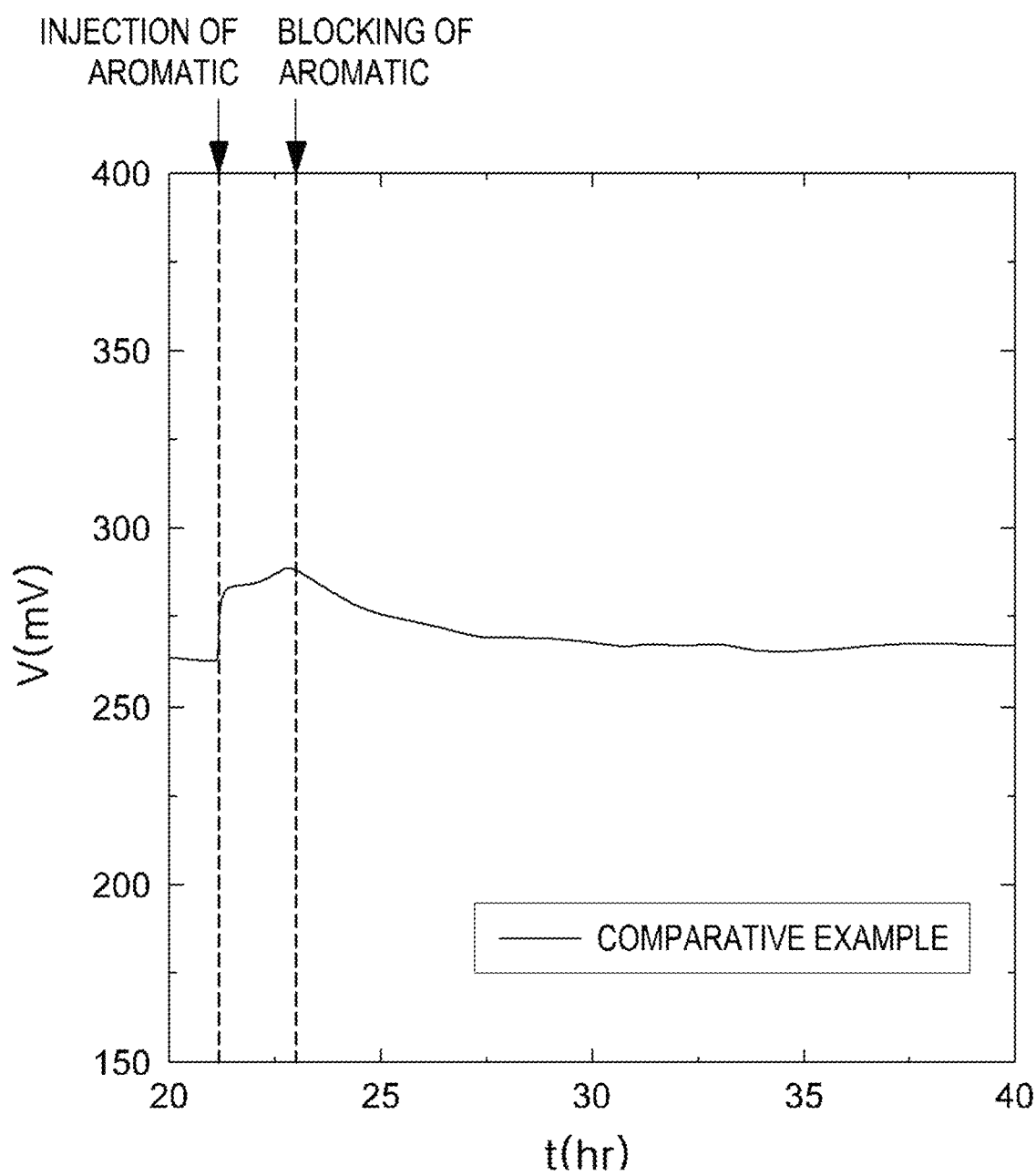
FIG. 11 is a graph illustrating voltage over time before and after Aromatic 2 is injected into the solid electrolyte-type carbon dioxide sensors in Comparative Example 1 being the related art.

FIG. 11 is a graph illustrating voltage over time before and after Aromatic 2 is injected into the solid electrolyte-type carbon dioxide sensors in Comparative Example 1 being the related art. The ambient conditions during the evaluation procedure are as follows: the concentration of carbon dioxide is 400 ppm, and the relative humidity is 50%. It can be confirmed that at the instance when Aromatic 2 is injected, the voltage is increased by approximately 50 mV or more, and the increase corresponds to the fact that the concentration of carbon dioxide is underestimated to approximately one tenth. Furthermore, it can be confirmed that Comparative Example 1 is not suitable as a solid electrolyte-type carbon dioxide sensor because Aromatic 2 is blocked from being injected and simultaneously, the voltage is gradually decreased without being suddenly decreased.

Figure 12:
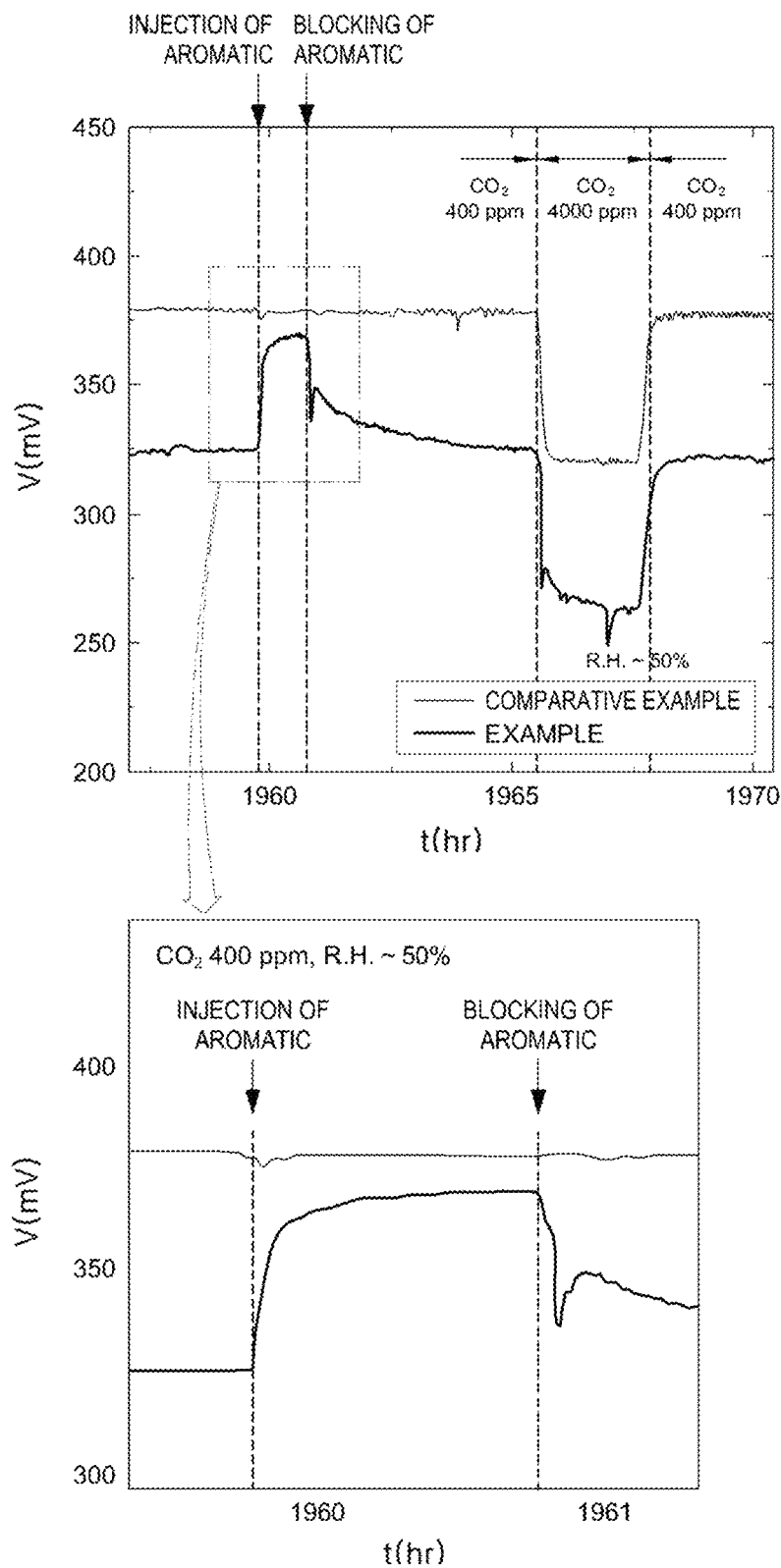
FIG. 12 is a graph illustrating voltage over time before and after Aromatic 2 is injected into the solid electrolyte-type carbon dioxide sensors in Comparative Example 2 being the related art and the Example of the present invention, and a partially enlarged view thereof.

FIG. 12 is a graph illustrating voltage over time before and after Aromatic 2 is injected into the solid electrolyte-type carbon dioxide sensors in Comparative Example 2 being the related art and the Example of the present invention, and a partially enlarged view thereof. The ambient conditions during the evaluation procedure are as follows: the concentration of carbon dioxide is 400 ppm, and the relative humidity is 50%. It can be confirmed that when Aromatic 2 is injected, the Example of the present invention has nearly no change in voltage, whereas Comparative Example 2 being the related art has an increase in voltage by approximately 50 mV or more. Furthermore, it can be confirmed that even at the instance when Aromatic 2 is blocked from being injected, the Example of the present invention has no change in voltage, whereas Comparative Example 2 being the related art has a voltage which gradually returns to the voltage before Aromatic 2 is injected. That is, when the partially enlarged view in FIG. 12 is examined, the difference can be very clearly confirmed, and it can be confirmed that the Example of the present invention has nearly no influence from the volatile organic compounds. Further, thereafter, it can be confirmed that when the concentration of carbon dioxide is increased from approximately 400 ppm to approximately 4,000 ppm, the Example of the present invention has a decreased voltage, and as a result, the concentration of carbon dioxide may be accurately measured, but in Comparative Example 2 being the related art, the voltage is decreased, but is not decreased steadily nor maintained at a predetermined voltage, and as a result, the accuracy of the solid electrolyte-type carbon dioxide sensor is decreased.

The present invention includes an oxidation catalyst to reduce an influence of voltage organic compounds on a solid electrolyte-type gas sensor, thereby improving the sensing performance of the sensor. That is, in a solid electrolyte-type carbon dioxide sensor including no oxidation catalyst, which is the related art, volatile organic compounds react with oxygen atoms adsorbed onto the surface of the detecting electrode, and thus decrease the concentration of the oxygen atoms adsorbed, and for the present reason, there is a problem in that the concentration of carbon dioxide is underestimated. In contrast, the solid electrolyte-type carbon dioxide sensor having a reduced influence from VOCs according to an exemplary embodiment of the present invention includes an oxidation catalyst, and as a result, the amount of carbon dioxide generated by reacting volatile organic compounds generated under general vehicle aromatic conditions of several to several tens of ppm or less with the oxidation catalyst is relatively smaller than the concentration of carbon dioxide in the atmosphere, that is, 400 ppm, so that there is an advantage in that the accuracy of the sensor is improved because no change in voltage occurs. Furthermore, a carbon dioxide sensor in another mode, as an example, the case of being combined with the NDIR mode has an advantage in that the concentration of volatile organic compounds can be quantitatively measured.

For convenience in explanation and accurate definition in the appended claims, the terms "upper", "lower", "inner", "outer", "up", "down", "upwards", "downwards", "front", "rear", "back", "inside", "outside", "inwardly", "outwardly", "interior", "exterior", "forwards", and "backwards" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A solid electrolyte-type $CO_2$ sensor having a reduced influence from volatile organic compounds (VOCs), the sensor comprising:
   a solid electrolyte;
   a reference electrode which is formed at a first side of the solid electrolyte;
   a detecting electrode of which a first side is joined and which is formed at a second side of the solid electrolyte;
   a substrate which is formed at a second side of the reference electrode; and
   an oxidation catalyst which is formed at a second side of the detecting electrode,
   wherein the oxidation catalyst is a metal catalyst.

2. The solid electrolyte-type $CO_2$ sensor of claim 1, wherein the reference electrode is a mixture of Li(Na)—Ti(Fe)—O or Pt.

3. The solid electrolyte-type $CO_2$ sensor of claim 1, wherein the detecting electrode is any one of $A_2CO_3$ or a mixture of $A_2CO_3$ and $BCO_3$,
   A is Li or Na, and B is Ba, Ca, or Sr.

4. The solid electrolyte-type $CO_2$ sensor of claim 1, wherein the solid electrolyte is $Na_{1+x}Zr_2Si_xP_{3-x}O_{12}$, and $0<X<3$.

5. The solid electrolyte-type $CO_2$ sensor of claim 1, wherein the solid electrolyte is $Li_{2+2x}Zn_{1-x}GeO_4$, and $0<X<1$.

6. The solid electrolyte-type $CO_2$ sensor of claim 1, wherein the substrate is alumina or mullite.

7. The solid electrolyte-type $CO_2$ sensor of claim 1, wherein the metal catalyst includes any one or more of Pt, Rh, or Pd.

8. The solid electrolyte-type $CO_2$ sensor of claim 1, wherein the oxidation catalyst is a supported catalyst in which a metal is supported on ceramic powder.

9. The solid electrolyte-type $CO_2$ sensor of claim 1, wherein the supported metal has a BET of 80 to 300 $m^2/g$.

10. The solid electrolyte-type $CO_2$ sensor of claim 8, wherein a thickness of the ceramic powder applied is three times or more than a particle size of the supported metal, and is 1,000 μm or less.

11. The solid electrolyte-type $CO_2$ sensor of claim 8, wherein a weight of the supported metal is 0.5 wt % or more based on a weight of the supported catalyst.

12. The solid electrolyte-type $CO_2$ sensor of claim 8, wherein a ceramic powder of the supported catalyst is any one of $Al_2O_3$, $ZrO_2$, $CeO_2$, $TiO_2$, zeolite, or a mixture thereof, and the metal is any one of Pt, Rh, Pd, or a mixture thereof.

13. The solid electrolyte-type $CO_2$ sensor of claim 1, wherein the oxidation catalyst seals the detecting electrode.

14. The solid electrolyte-type $CO_2$ sensor of claim 1, wherein the reference electrode is joined and sealed by bonding the solid electrolyte to the substrate.

* * * * *